US008700345B2

(12) United States Patent
Okabayashi (10) Patent No.: US 8,700,345 B2
(45) Date of Patent: Apr. 15, 2014

(54) AUTOMATIC ANALYZER (75) Inventor: Osamu Okabayashi, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 323 days.

(21) Appl. No.: 13/139,924

(22) PCT Filed: Mar. 19, 2009

(86) PCT No.: PCT/JP2009/055506
§ 371 (c)(1),
(2), (4) Date: Jun. 15, 2011

(87) PCT Pub. No.: WO2010/079629
PCT Pub. Date: Jul. 15, 2010

(65) Prior Publication Data
US 2011/0257908 A1 Oct. 20, 2011

(30) Foreign Application Priority Data
Jan. 9, 2009 (JP) ................................. 2009-003962

(51) Int. Cl.
*G06F 19/00* (2011.01)
(52) U.S. Cl.
USPC ................ 702/50; 702/19; 702/25; 250/573; 250/576; 436/10; 422/50
(58) Field of Classification Search
USPC .................. 702/19, 25, 50; 422/50; 250/573, 250/576–577, 227.25
See application file for complete search history.

(56) References Cited

U.S. PATENT DOCUMENTS 5,473,551 A * 12/1995 Sato et al. ......................... 702/19
7,027,935 B2 * 4/2006 Shimase et al. .................. 702/47
2011/0125415 A1 * 5/2011 Mitsuyama et al. ............. 702/25

FOREIGN PATENT DOCUMENTS

JP          59-147626 A      8/1984
JP           1-134234 A      5/1989
JP         2007-198739 A     8/2007

OTHER PUBLICATIONS

The International Search Report from PCT/JP2009/055506, mailed Apr. 28, 2009, included English Translation, 1 page.
Japanese Office Action mailed on Mar. 26, 2013 for JP Application No. 2009-003962, 3 pages.

* cited by examiner

*Primary Examiner* — Jonathan C. Teixeira Moffat
*Assistant Examiner* — Hien Vo
(74) *Attorney, Agent, or Firm* — Kilpatrick Townsend & Stockton LLP (57) ABSTRACT

An automatic analyzer, capable of obtaining analysis results using reaction liquids with absorbance appropriate for analysis processing, is provided. To that end, the analyzer includes: a standard deviation calculating section for calculating a standard deviation of absorbances of a reaction liquid, measured by a photometry section at any one time a reaction container passes through the photometry section, every time the reaction container passes through the photometry section; a standard deviation judging section for judging whether each standard deviation calculated by the standard deviation calculating section is smaller than a threshold set based on a standard deviation of absorbances of a homogeneously-stirred reaction liquid; and an absorbance determining section for determining any of average values of a plurality of absorbances with a standard deviation judged smaller than the threshold by the standard deviation judging section, calculated by the average value calculating section, as absorbance for sample analysis.

4 Claims, 9 Drawing Sheets

AUTOMATIC ANALYZER

CROSS-REFERENCE TO RELATED APPLICATION

This application is a National Stage of International Application No. PCT/JP2009/055506, filed Mar. 19, 2009, which claims the benefit of priority to Japanese Application No. 2009-003962, filed Jan. 9, 2009, the disclosures of each are herein incorporated by reference.

TECHNICAL FIELD

The present invention relates to an automatic analyzer for dispensing a sample and a reagent into a reaction container and measuring absorbance of the reaction liquid produced in the reaction container to analyze the sample.

BACKGROUND ART

Conventionally, automatic analyzers, for dispensing a sample and a reagent into a reaction container and measuring absorbance of the reaction liquid produced in the reaction container to analyze the sample, have been known. Such an automatic analyzer includes a photometry section with a light source and a light receiving section. The light source irradiates light onto a reaction container containing a reaction liquid, and the light receiving section calculates the absorbance based on the amount of light transmitted through the reaction liquid in the reaction container and received by the light receiving section, thereby analyzing the sample.

One of the methods for calculating absorbance is as follows: every time a reaction container passes through a photometry section, the photometry section successively irradiates light onto a plurality of measurement points on the reaction container, and the photometry section receives the light transmitted through the reaction liquid and averages the received light in order to calculate the absorbance of the reaction liquid. Through this method, it is possible to prevent variations in the amount of light for each measurement point to calculate absorbance. However, there has been a case when there is any measurement point in which a sample and a reagent are not mixed with each other sufficiently, or any measurement point in which a foreign substance or the like is mixed with the reaction liquid, light to be transmitted through the reaction liquid is blocked because of such a measurement point, and as a result, the amount of light is reduced at the measurement point and absorbance is thus calculated to be a value higher than the actual value.

Thus, another automatic analyzer is known in which a prominent amount of light, different from the amount of light in an ordinary chemical reaction, at a measurement point is excluded among a plurality of measurement points, and the amounts of light of the rest of the measurement points are averaged to calculate absorbance (see Patent Reference 1)
Patent Reference 1: Japanese Laid-Open Publication No. 2007-198739

DISCLOSURE OF THE INVENTION

Problems to be Solved by the Invention

The automatic analyzer according to Patent Reference 1, however, merely excludes an abnormal measurement of light and calculates absorbance based on the remaining light measurements. Therefore, it is not always possible to obtain an accurate analysis result from the calculated absorbance.

The present invention is intended to solve the problems described above. It is an object of the present invention to provide an automatic analyzer capable of obtaining an accurate analysis result even in a case where there is an abnormal measurement point existing among a plurality of measurement points for measuring absorbance of a reaction liquid.

Means for Solving the Problem

An automatic analyzer according to the present invention for analyzing a sample by dispensing the sample and a reagent into a reaction container and using a reaction liquid combined in the reaction container, includes: a reaction table for retaining a plurality of the reaction containers along the circumference, capable of rotating along the circumference; a photometry section for measuring absorbance of the reaction liquid in the reaction container a plurality of times at any one time the reaction container passes through a predetermined area with the rotation of the reaction table, which is performed every time the reaction container passes through the predetermined area; a standard deviation calculating section for calculating the standard deviation of a plurality of absorbances of the reaction liquid measured by the photometry section at any one time the reaction container passes through the predetermined area, which is performed every time the reaction container passes through the predetermined area; a standard deviation judging section for judging as to whether or not each of a plurality of the standard deviations calculated by the standard deviation calculating section is smaller than the threshold set based on the standard deviation of a plurality of absorbances in a homogeneously-stirred reaction liquid; an average value calculating section for calculating an average value for the plurality of absorbances for the reaction liquid having a standard deviation judged to be smaller than the threshold by the standard deviation judging section; and an absorbance determining section for determining any one of a plurality of average values calculated by the average value calculating section to be absorbance for performing a sample analysis, thereby achieving the object described above.

In one embodiment, in the automatic analyzer according to the present invention, the absorbance determining section determines absorbance when the plurality of standard deviations decrease over time and the number of standard deviations smaller than the threshold is 2 or more.

In another embodiment, the automatic analyzer according to the present invention further includes an abnormality specifying section for specifying a cause of abnormality based on the change over time in the plurality of standard deviations.

In yet another embodiment, in the automatic analyzer according to the present invention, the abnormality specifying section specifies that the reaction liquid of the reaction container is abnormal when the number of the standard deviations smaller than the threshold is 1 or below.

Effects of the Invention

The automatic analyzer according to the present invention calculates a standard deviation of a plurality of absorbances of a reaction liquid every time a reaction container passes through a predetermined area, the absorbances being measured by a photometry section at any one time the reaction container passes through the predetermined area with the rotation of a reaction table; and the automatic analyzer judges as to whether or not each of the plurality of calculated standard deviations is smaller than a threshold set based on a standard deviation of a plurality of absorbances of a homogeneously-stirred reaction liquid. Subsequently, the automatic analyzer calculates an average value of the plurality of absorbances of the reaction liquid having a standard deviation judged to be smaller than the threshold, and determines any one of the plurality of average values to be the absorbance used to perform a sample analysis. As a result, it allows one to obtain an analysis result by using a reaction liquid having an absorbance appropriate for analysis processing.

DESCRIPTION OF THE REFERENCE NUMERALS 1 automatic analyzer
2 measurement mechanism
3 control mechanism
11a sample container
11b sample rack
12 sample dispensing mechanism
13 reaction table
14 reagent repository
15 reagent container
16 reagent dispensing mechanism
17 stirring section
18 photometry section
18a light source
18b light receiving section
18c A/D converter
19 washing section
20 reaction container
20a, 20b side wall
20c bottom wall
20d liquid retaining part
20e opening
31 control section
32 input section
33 analysis section
34 determination section
34a standard deviation calculating section
34b standard deviation judging section
34c average value calculating section
34d absorbance determining section
34e abnormality specifying section
34f report processing section
35 recording section
36 output section
37 transmission and reception section
Am photometric region
BL analysis light
W reaction liquid
S1 solid matter
S2 scratch

BEST MODE FOR CARRYING OUT THE INVENTION

Hereinafter, a preferred embodiment of an automatic analyzer according to the present invention will be described with reference to the accompanying figures. It should be noted that the present invention is not limited to the following embodiment. It should be also noted that identical portions are given the same reference numerals in the description of the figures.

Figure 1:
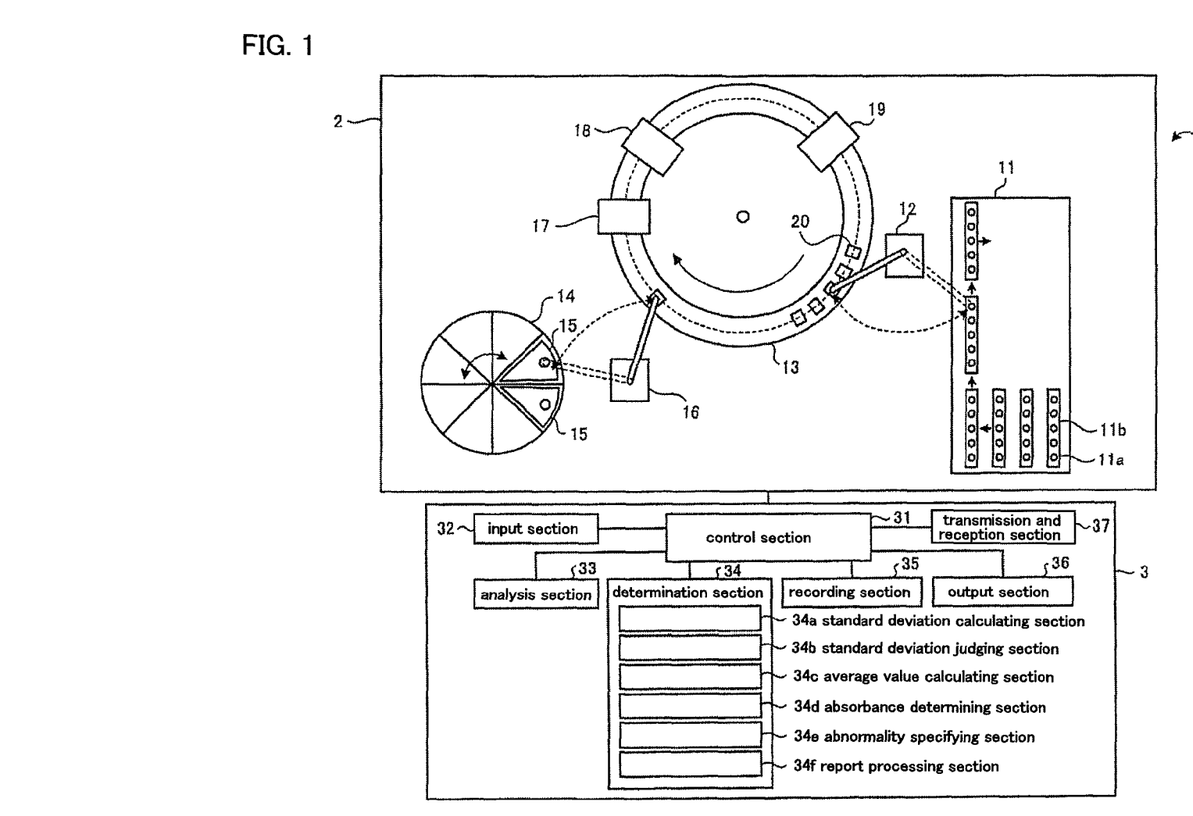
FIG. 1 is a schematic view illustrating a diagrammatic configuration of an automatic analyzer according to an embodiment of the present invention.

FIG. 1 is a schematic view illustrating a diagrammatic configuration of an automatic analyzer according to the embodiment of the present invention. As illustrated in FIG. 1, an automatic analyzer 1 according to the embodiment of the present invention includes: a measurement mechanism 2 for dispensing a reagent and a sample into a reaction container 20, combining the reagent and the sample within the reaction container 20, and measuring the absorbance of the reaction liquid; and a control mechanism 3 for controlling the overall automatic analyzer 1 including the measurement mechanism 2 as well as controlling the analysis of a measurement result from the measurement mechanism 2. The automatic analyzer 1 automatically analyzes a plurality of samples by the cooperation of the two mechanisms.

First, the measurement mechanism 2 will be described. As illustrated in FIG. 1, the measurement mechanism 2 includes: a sample transferring section 11 for successively transferring a sample rack 11b in the arrowed direction in the figure, where the sample rack 11b retains a plurality of sample containers 11a containing a sample, such as blood and urine; a sample dispensing mechanism 12 for dispensing, into a reaction container 20, a sample contained in the sample container 11a being at rest at a predetermined position of the sample transferring section 11; a reaction table 13 for retaining a plurality of reaction containers 20 along the circumference, and for rotating in the arrowed direction in the figure to transfer the reaction containers 20 to a predetermined position; a reagent repository 14 for housing a plurality of reagent containers 15 in which a reagent to be dispensed into a reaction container 20 is contained; a reagent dispensing mechanism 16 for dispensing, into a reaction container 20, a reagent contained in a reagent container 15 being at rest at a predetermined position within the reagent repository 14; a stirring section 17 for stirring a sample and a reagent dispensed in a reaction container 20; a photometry section 18 for measuring absorbance of a liquid dispensed in a reaction container 20; and a washing section 19 for washing a reaction container 20 after a measurement is completed by the photometry section 18.

Next, the control mechanism 3 will be described. The control mechanism 3 includes: a control section 31; an input section 32; an analysis section 33; a determination section 34; a recording section 35; an output section 36; and a transmission and reception section 37. The input section 32, analysis section 33, determination section 34, recording section 35, output section 36 and transmission and reception section 37 are electrically connected with the control section 31.

The control section 31 is actualized with a CPU and the like, and controls the processing and operation of respective sections of the automatic analyzer 1. The control section 31 performs given processing on information input from respective constituent sections of the automatic analyzer 1, and also outputs the information, which has been through given processing, to the respective constituent sections.

The input section 32 is actualized with a keyboard, a mouse, a touch panel with input and output functions, and the like, and acquires various kinds of information necessary for a sample analysis, instruction information for an analysis operation, and the like from the outside.

The analysis section 33 performs analysis of a component of a sample, or the like, based on a measurement result of absorbance measured by the photometry section 18.

The determination section 34 determines any one of a plurality of absorbances measured by the photometry section 18 to be the absorbance used for the sample analysis. The determination section 34 includes: a standard deviation calculating section 34a; a standard deviation judging section 34b; an average value calculating section 34c; an absorbance determining section 34d; an abnormality specifying section 34e; and a report processing section 34f. The standard deviation calculating section 34a calculates a standard deviation of a plurality of absorbances of a reaction liquid every time a reaction container 20 passes through the photometry section 18, the absorbances being measured by the photometry section 18 at any one time the reaction container 20 passes through the photometry section 18. The standard deviation judging section 34b judges as to whether or not each of a plurality of standard deviations calculated by the standard deviation calculating section 34a is smaller than the threshold set based on a standard deviation of a plurality of absorbances of a homogeneously-stirred reaction liquid. The average value calculating section 34c calculates an average value of a plurality of absorbances of a reaction liquid measured by the photometry section 18 at any one time a reaction container 20 passes through the photometry section 18, the reaction container 20 having a standard deviation judged to be smaller than the threshold set based on the standard deviation of the plurality of absorbances of the homogeneously-stirred reaction liquid by the standard deviation judging section 34b. The absorbance determining section 34d determines any one of a plurality of average values calculated by the average value calculating section 34c to be the absorbance used for performing the analysis of a sample. The abnormality specifying section 34e specifies a cause of abnormality based on a chronological change in the standard deviation of a plurality of absorbances of the reaction liquid measured by the photometry section 18 at any one time a reaction container 20 passes through the photometry section 18, the standard deviation being calculated by the standard deviation calculating section 34a. The report processing section 34f outputs information indicating a cause of abnormality specified by the abnormality specifying section 34e, through the control section 31 to the output section 36.

The recording section 35 is actualized with a hard disk for magnetically storing information; and a memory for loading, and electrically storing, various programs from the hard disk when the automatic analyzer 1 performs processing, the programs being associated with the processing. The recording section 35 stores various pieces of information including an analysis result of a sample and the like. The recording section 35 may include a supplemental storing apparatus capable of reading information stored on a storage medium, such as CD-ROM, DVD-ROM, PC card and the like.

The output section 35 is constituted of a display, a printer, a speaker and the like, for outputting various kinds of information.

The transmission and reception section 37 has a function as an interface for transmitting and receiving information in accordance with a predetermined format via a communication network (not shown).

In the automatic analyzer 1 as configured above, the reagent dispensing mechanism 16 dispenses a reagent, from a reagent container 15 of the reagent repository 14, into a plurality of reaction containers 20 successively transferred on the reaction table 13. Subsequently, the sample dispensing mechanism 12 dispenses a sample from a sample container 11a at a sample suction position. Subsequently, the photometry section 18 measures absorbance of a reaction liquid obtained by combining the reagent and the sample, and the analysis section 33 performs analysis based on the measurement result, thereby performing a component analysis of a sample or the like automatically. Subsequently, the washing section 19 washes the reaction container 20, which is conveyed after the measurement by the photometry section 18 is completed, while the reaction container 20 is being conveyed.

Figure 2:
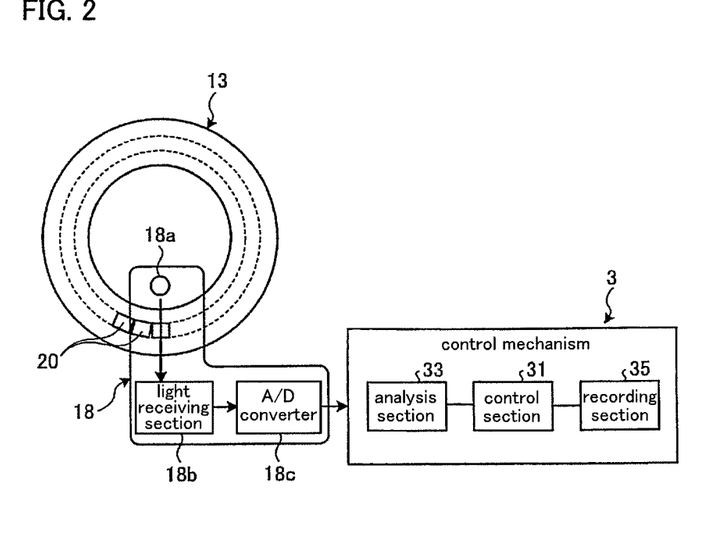
FIG. 2 is a schematic view illustrating a diagrammatic configuration of a photometry section according to an embodiment of the present invention.
Figure 3:
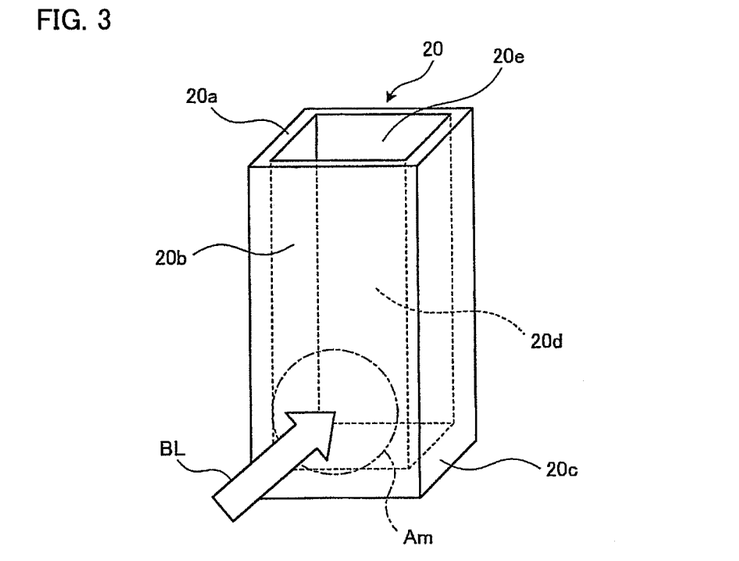
FIG. 3 is a perspective view of a reaction container according to an embodiment of the present invention.

Next, the photometry section 18 and the reaction container 20 will be described. FIG. 2 is a schematic view illustrating a diagrammatic configuration of the photometry section 18. FIG. 3 is a perspective view of the reaction container. As illustrated in FIG. 2, the photometry section 18 includes: a light source 18a; a light receiving section 18b; and an A/D converter 18c. The light source 18a and light receiving section 18b are positioned at positions facing each other, with a reaction container 20 retained by the reaction table 13 interposed therebetween. The light source 18a is positioned on the side closer to the internal circumference of the reaction table 13. The light receiving section 18b is positioned on the side closer to the external circumference of the reaction table 13. The light source 18a is actualized with a halogen lamp or the like, and irradiates light for analysis onto a reaction container 20. The light receiving section 18b has: a diffraction grating, such as a concave surface diffraction grating; a light receiving element array for measuring light separated by the diffraction grating for each spectrum determined by a measurement category, and outputting a signal corresponding to the amount of light thereof; and a light receiving sensor, such as a CCD sensor and a CMOS sensor. The A/D converter 18c converts a signal output from the light receiving section 18b into a digital value, and outputs the digital value to the control section 31.

As illustrated in FIG. 3, the reaction container 20 is a very small container with a volume of several nL to several mL. A liquid retaining part 20d for retaining a liquid is formed with a side wall 20a, a side wall 20b and a bottom wall 20c, and an opening 20e lies above the liquid retaining part 20d. For the reaction container 20, a transparent material, such as glass including heat-resistant glass, or synthetic resin including cyclic olefin and polystyrene, is used to transmit 80% or more of light contained in an analysis light BL (340 nm to 380 nm) irradiated from the light source 18a of the photometry section 18. The reaction container 20 is positioned such that the side wall 20b faces the radius direction of the reaction table 13. In addition, when the reaction container 20 passes through the analysis light BL irradiated by the light source of the photometry section 18 with the rotation of the reaction table 13, the bottom portion of the side wall 20b is used as a photometric region Am, through which the analysis light BL passes.

Figure 4:
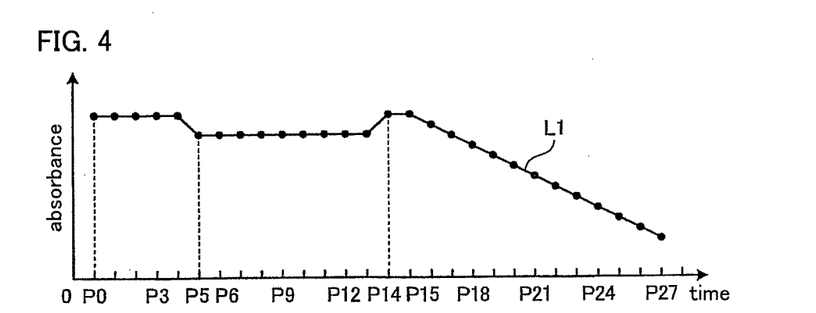
FIG. 4 is a graph illustrating the change over time in absorbance measured by a photometry section every time a reaction container passes in between a light source and a light receiving section.

FIG. 4 is a graph illustrating the change over time in absorbance measured by the photometry section 18 every time a reaction container 20 passes in between the light source 18a and the light receiving section 18b. The curved line L1 illustrated in FIG. 4 indicates the change over time in absorbance measured by the photometry section 18 every time a reaction container 20, containing a reaction liquid, passes in between the light source 18a and the light receiving section 18b. In addition, the axis of abscissas indicates time while the axis of ordinates indicates absorbance. Herein, the time at which the reaction container 20 passes in between the light source 18a and the light receiving section 18b is indicated as a photometry point Pn (where n=0, 1 . . . 27).

As illustrated in FIG. 4, the photometry section 18 measures absorbance twenty-eight times in total for each reaction container 20, including the absorbance of a liquid in the reaction container 20 after the dispensing of a first reagent, and through the dispensing of a sample and the dispensing of a second reagent. More specifically, the photometry point P0 indicates absorbance immediately after the dispensing of the first reagent, while the photometry point P5 indicates absorbance immediately after the dispensing of the sample and the photometry point P14 indicates absorbance immediately after the dispensing of the second reagent. The analysis section 33 analyzes the sample based on the absorbance after the elapse of a predetermined time from the time at which the absorbance was measured when the second reagent was dispensed into the reaction container 20. More specifically, as illustrated in FIG. 4, the sample is analyzed based on the gradient of the absorbance, or the change in values of absorbances, per unit time based on the absorbances at the photometry points P14 to P27.

Figure 5:
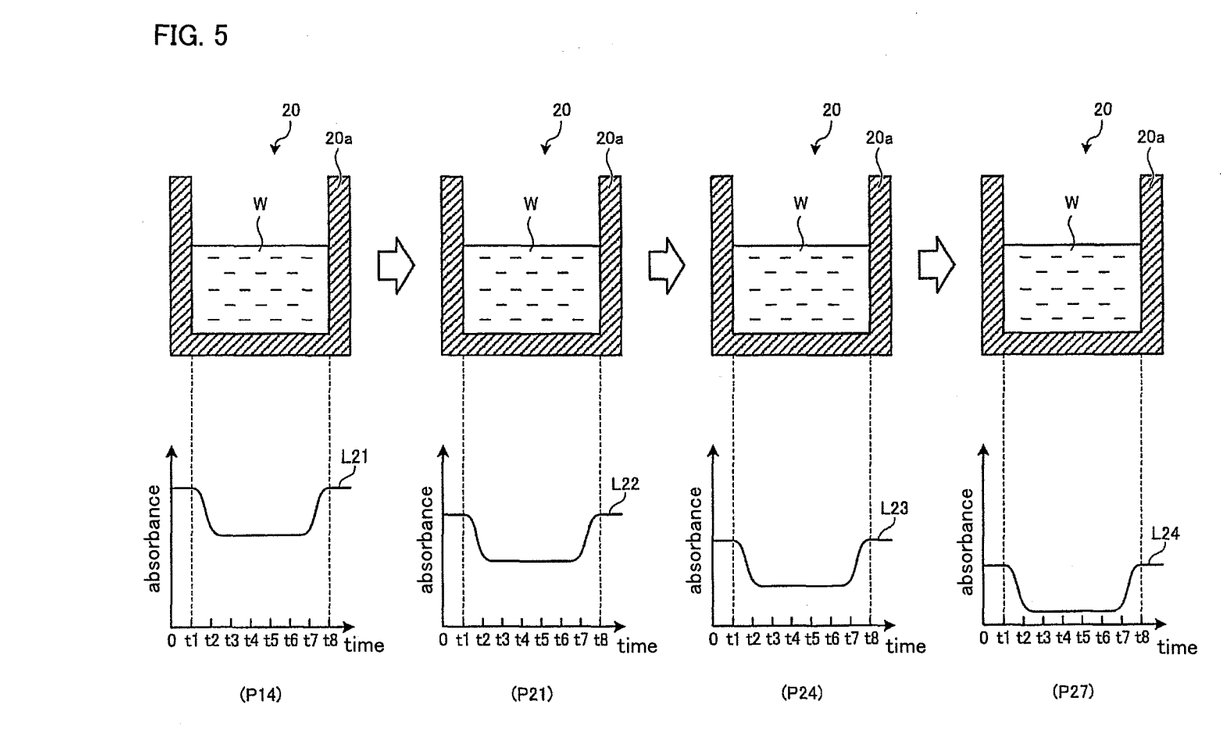
FIG. 5 is a graph illustrating the change over time in absorbance of a reaction liquid measured a plurality of times by a photometry section at any one time a reaction container passes in between a light source and a light receiving section.

FIG. 5 is a graph illustrating the change over time in absorbance of a reaction liquid W measured a plurality of times by the photometry section 18 at any one time a reaction container 20 passes in between the light source 18a and the light receiving section 18b. The curved lines L21, L22, L23 and L24 respectively indicate the change over time at photometry points P14, P21, P24 and P27, illustrating a case where the stirring state of the reaction liquid W is favorable. Note that in FIG. 5, the intervals of time points to (where n=1, 2 . . . 8) described in the time axis are all constant with Δt.

As illustrated in FIG. 5, the reaction liquid W in the reaction container 20 passes through the photometry section 18 during the time t1 to time t8 with the rotation of the reaction table 13. The absorbance measured by the photometry section 18 during this period is less than the absorbance measured by the photometry section 18 when the side wall 20a passes by, and the absorbance indicates a substantially constant value. In addition, as the curved lines L21 to L24 indicate, the change in the absorbance at respective photometry points is a substantially constant change, and the value of the absorbance decreases as the time advances. The time t8−t1=7Δt, during which the reaction container 20 passes through the photometry section 18, varies depending on the speed of rotation of the reaction table 13. The speed of rotation of the reaction table 13 is defined in accordance with the performance of the A/D converter 18c.

Figure 6:
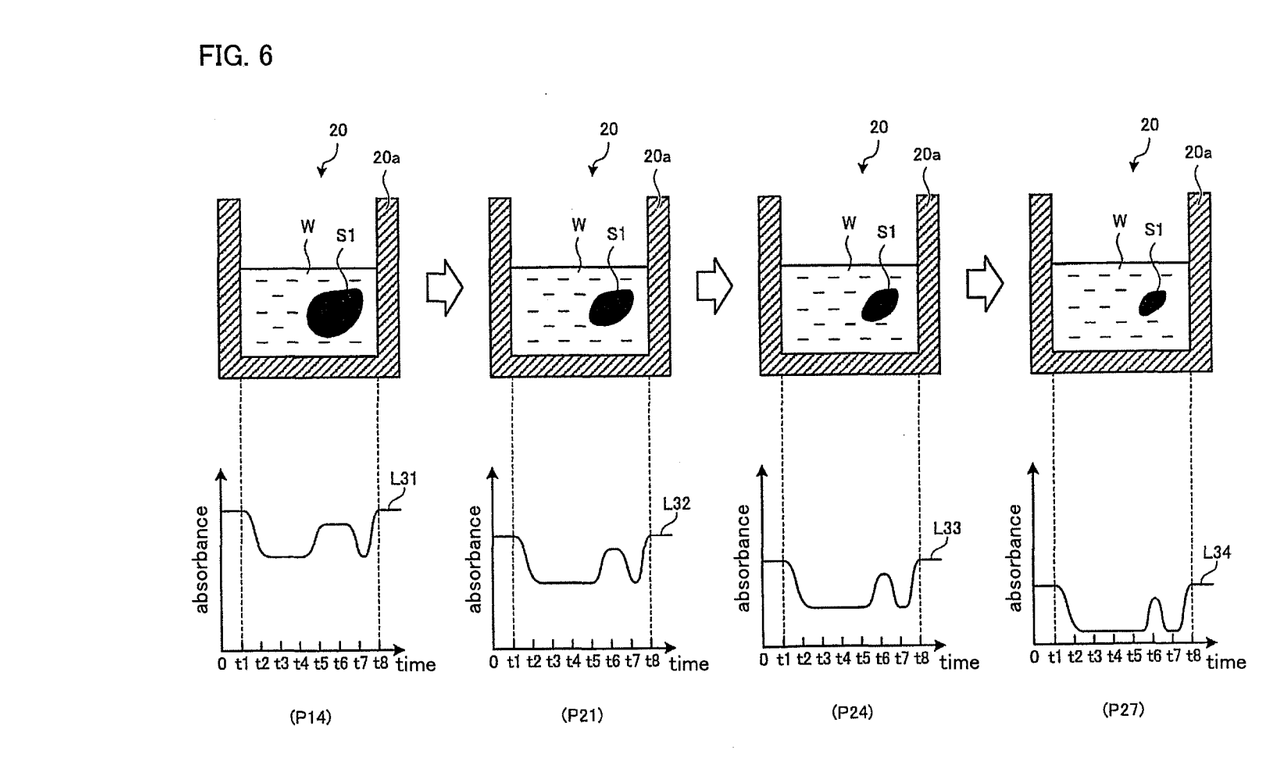
FIG. 6 is a graph illustrating the change over time in absorbance of a reaction liquid measured a plurality of times by a photometry section at any one time a reaction container passes in between a light source and a light receiving section, where the reaction liquid contains a portion in which a sample and a reagent are not well mixed with each other.

FIG. 6 is a graph illustrating the change over time in absorbance of a reaction liquid W measured a plurality of times by the photometry section 18 at any one time a reaction container 20 passes in between the light source 18a and the light receiving section 18b, where the reaction liquid W contains a portion S1 in which a sample and a reagent are not well mixed with each other. The curved lines L31 to L34 illustrated in FIG. 6 indicate the change over time in absorbance of the reaction liquid W measured a plurality of times by the photometry section 18 at any one time a reaction container 20 passes in between the light source 18a and the light receiving section 18b, where the reaction liquid W contains a portion S1 in which a sample and a reagent are not well mixed with each other.

As illustrated in FIG. 6, in a case where there is the portion S1, in which a sample and a reagent are not well mixed with each other, existing due to the stirring state of the reaction liquid W, the portion S1, in which a sample and a reagent are not well mixed with each other, blocks or absorbs the analysis light BL. As a result, the amount of light passing through the reaction liquid W is reduced. Thus, as illustrated by the curved lines L31 to L34, the time during which the portion S1, in which a sample and a reagent are not well mixed with each other, exists at anyone time the reaction container 20 passes in between the light source 18a and the light receiving section 18b, or more specifically, the time of the curved line L31 at the photometry point P14, is as long as the time point t5−t7=2Δt. The absorbance during this time indicates a high value. Subsequently, since the reaction liquid W in the reaction container 20 is stirred by the moving and stopping of the reaction table 13, the portion S1, in which a sample and a reagent are not well mixed with each other, is reduced as the photometry points advance. Accordingly, every time the reaction container 20 passes by the light source 18a and the light receiving section 18b, the time during which the sample and the reagent are not well mixed with each other is also shortened gradually. More specifically, in a comparison between the curved line L31 at the photometry point P14 and the curved line L34 at the photometry point P27, the time during which the sample and the reagent are not well mixed with each other in the curved line L31 is as long as the time point t5−t7=2Δt. On the other hand, the time during which the sample and the reagent are not well mixed with each other in the curved line L34 is as long as the time point t6−t7=Δt, which is shorter. In this case, although the time, during which the sample and the reagent are not well mixed with each other, is getting shorter with the lapse in time, it does not mean that the reaction liquid W is homogeneously mixed. Thus, the stirring state of the reaction liquid W is not favorable.

Figure 7:
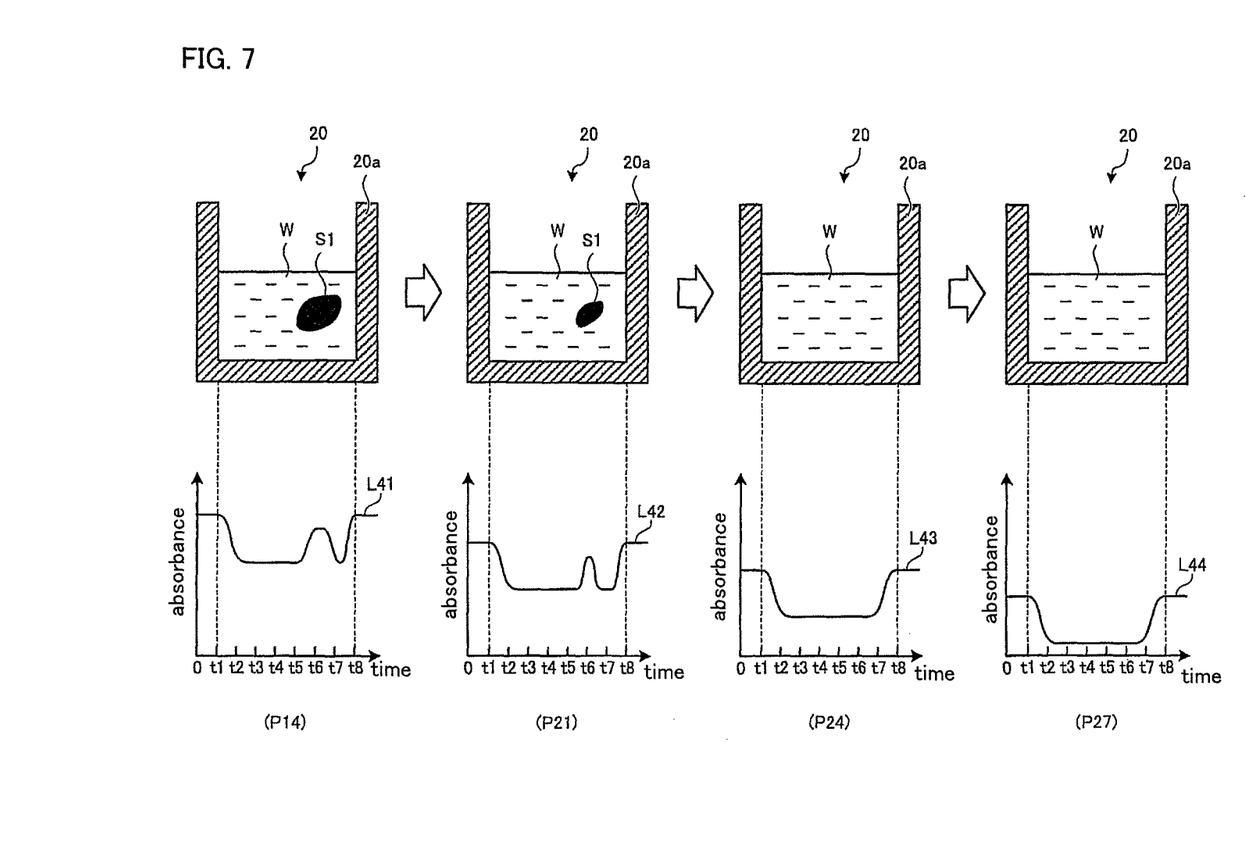
FIG. 7 is a graph illustrating the change over time in absorbance of a reaction liquid measured a plurality of times by a photometry section at any one time a reaction container passes in between a light source and a light receiving section, where the reaction liquid contains a portion in which a sample and a reagent are not well mixed with each other.

FIG. 7 is a graph illustrating the change over time in absorbance of a reaction liquid W measured a plurality of times by the photometry section 18 at any one time a reaction container 20 passes in between the light source 18a and the light receiving section 18b, where the reaction liquid W contains a portion S1 in which a sample and a reagent are not well mixed with each other. The curved lines L41 to L42 illustrated in FIG. 7 indicate the change over time in absorbance of the reaction liquid W measured a plurality of times by the photometry section 18 at any one time a reaction container 20 passes in between the light source 18a and the light receiving section 18b, where the reaction liquid W contains a portion S1 in which a sample and a reagent are not well mixed with each other. In addition, the curved lines L43 and L44 indicate the change over time in absorbance of the reaction liquid W measured a plurality of times by the photometry section 18 at anyone time the reaction container 20 passes in between the light source 18a and the light receiving section 18b, after the portion S1, in which the sample and the reagent are not well mixed with each other, has disappeared from the reaction liquid W.

As illustrated in FIG. 7, since the reaction liquid W in the reaction container 20 is stirred by the moving and stopping of the reaction table 13, the portion S1, in which the sample and the reagent are not well mixed with each other, is reduced, and the portion S1, in which the sample and the reagent are not well mixed with each other, disappears during the measurement. Thus, as illustrated by the curved lines L43 and L44, the change in the absorbance at the photometry points is indicated to be substantially constant every time the reaction container 20 passes in between the light source 18a and the light receiving section 18b, and the stirring state of the reaction liquid W becomes favorable.

Figure 8:
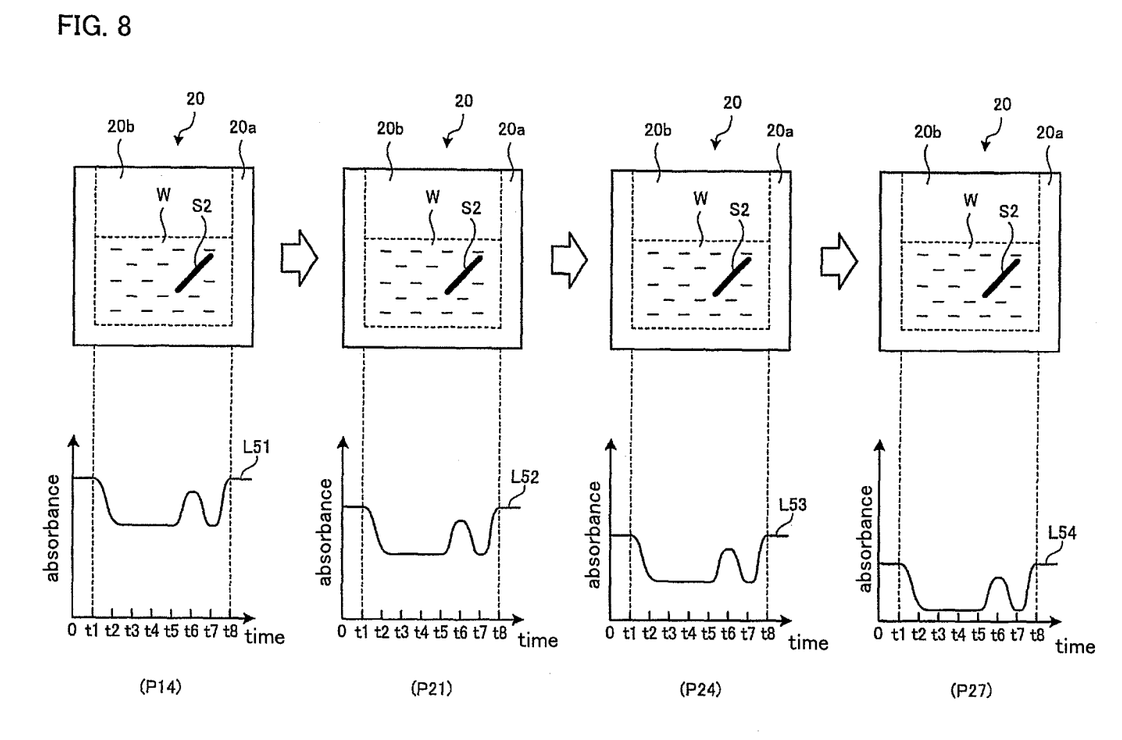
FIG. 8 is a graph illustrating the change over time in absorbance of a reaction liquid measured a plurality of times by a photometry section at any one time a reaction container passes in between a light source and a light receiving section, where there is a scratch existing on a side wall of the reaction container.

FIG. 8 is a graph illustrating the change over time in a reaction liquid W measured a plurality of times by the photometry section 18 at any one time a reaction container 20 passes in between the light source 18a and the light receiving section 18b, where there is a scratch S2 existing on the side wall 20b of the reaction container 20. The curved lines L51 to L54 illustrated in FIG. 8 indicate the change over time in the reaction liquid W measured a plurality of times by the photometry section 18 at any one time a reaction container 20 passes in between the light source 18a and the light receiving section 18b, where there is the scratch S2 existing on the side wall 20b of the reaction container 20.

As illustrated in FIG. 8, in a case where there is the scratch S2 existing on the side wall 20b of the reaction container 20, the scratch S2 reflects or blocks the analysis light BL, thus reducing the amount of light transmitted through the reaction liquid W. Thus, as illustrated by the curved lines L51 to L54, the time during which the scratch S2 exists at any one time the reaction container 20 passes in between the light source 18a and the light receiving section 18b is specifically as long as the time point t6–t7=Δt. The absorbance during this time indicates a high value. In this case, unless the reaction containers 20 are exchanged, the time during which the scratch S2 exists will not disappear. Even if the stirring state of the reaction liquid W is favorable, absorbance is measured to be a value higher than the actual value.

Although absorbance changes as time elapses in any of the cases described above, the way it changes varies. In other words, the standard deviation of a plurality of absorbances of the reaction liquid W measured by the photometry section 18 at any one time a reaction container 20 passes in between the light source 18a and the light receiving section 18b, is different in each case. In the following description, the standard deviation of a plurality of absorbances of the reaction liquid W measured by the photometry section 18 at any one time a reaction container 20 passes in between the light source 18a and the light receiving section 18b, will be simply referred to as a standard deviation of absorbance.

Figure 9:
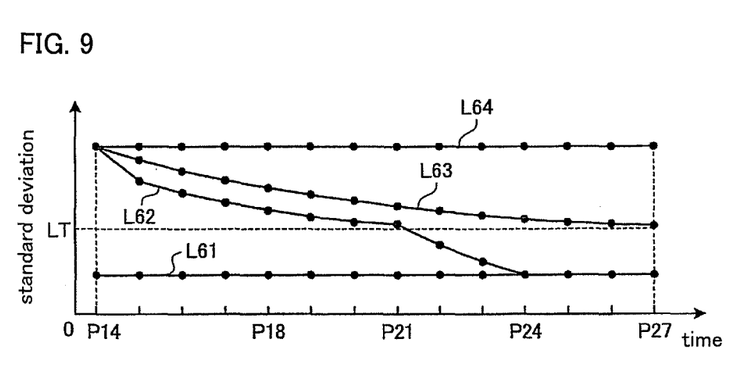
FIG. 9 is a graph illustrating the change over time in standard deviation of absorbance in accordance with the stirring state of a reaction liquid.

FIG. 9 is a graph illustrating the change over time in a standard deviation of absorbance in accordance with the stirring state of a reaction liquid W. In FIG. 9, the curved line L61 indicates the change over time in a standard deviation of absorbance when the stirring state of the reaction liquid W is favorable (which corresponds to FIG. 5). The curved line L62 indicates the change over time in a standard deviation of absorbance when the stirring state of the reaction liquid W becomes favorable in the course of the measurement (which corresponds to FIG. 7). The curved line L63 indicates the change over time in the standard deviation of absorbance when the stirring state of the reaction liquid W is not favorable (which corresponds to FIG. 6). The curved line L64 indicates the change over time in a standard deviation of absorbance when there is a scratch S2 existing on a side wall 20b of a reaction container 20 (which corresponds to FIG. 8). Note that the axis of abscissas refers to time, and the axis of ordinates refers to standard deviation.

When the stirring state of the reaction liquid W is favorable as illustrated in FIG. 9, every standard deviation of absorbance is smaller than a threshold LT at each photometry point, and a constant value is maintained between the photometry points P14 to P27, as illustrated by the curved line L61. When the stirring state of the reaction liquid W becomes favorable in the course of measurement, the standard deviation of absorbance at each photometry point decreases over time and becomes smaller than the threshold LT in the course of measurement, as illustrated by the curved line L62. When the stirring state of the reaction liquid W is not favorable, the standard deviation of absorbance at each photometry point decreases over time while exceeding the threshold LT, as illustrated by the curved line L63. When there is a scratch S2 existing on a side wall 20b of a reaction container 20, the standard deviation of absorbance at each photometry point maintains a constant value while exceeding the threshold LT, as illustrated by the curved line L64. Note that the threshold LT is set based on a standard deviation of a plurality of absorbances of a homogeneously-stirred reaction liquid W.

The standard deviation calculating section 34a calculates the standard deviation of absorbance every time a reaction container 20 passes in between the light source 18a and the light receiving section 18b. Subsequently, the standard deviation judging section 34b judges as to whether or not the standard deviation of absorbance at the photometry points P14 to P27 calculated by the standard deviation calculating section 34a is smaller than the threshold LT. The average value calculating section 34c calculates an average value of absorbances of the reaction liquid W in the reaction container 20, the reaction liquid W having a standard deviation of absorbance smaller than the threshold LT, measured a plurality of times by the photometry section 18 at any one time the reaction container 20 passes in between the light source 18a and the light receiving section 18b. Subsequently, the absorbance determining section 34d determines anyone of a plurality of average values calculated by the average value calculating section 34c, to be the absorbance used for performing the sample analysis. More specifically, the absorbance used for performing the sample analysis is determined in accordance with an analysis method, an analysis category, a reagent or the like. In addition, the abnormality specifying section 34e specifies a cause of abnormality based on the chronological change in the standard deviation of absorbance. More specifically, when the standard deviation of absorbance exceeds the threshold LT and decreases through the photometry points P14 to P27, the stirring state of the reaction liquid W is specified to be unfavorable; and when the standard deviation of absorbance exceeds the threshold LT and maintains a constant value through the photometry points P14 to P27, the reaction container 20 is specified to be abnormal.

Figure 10:
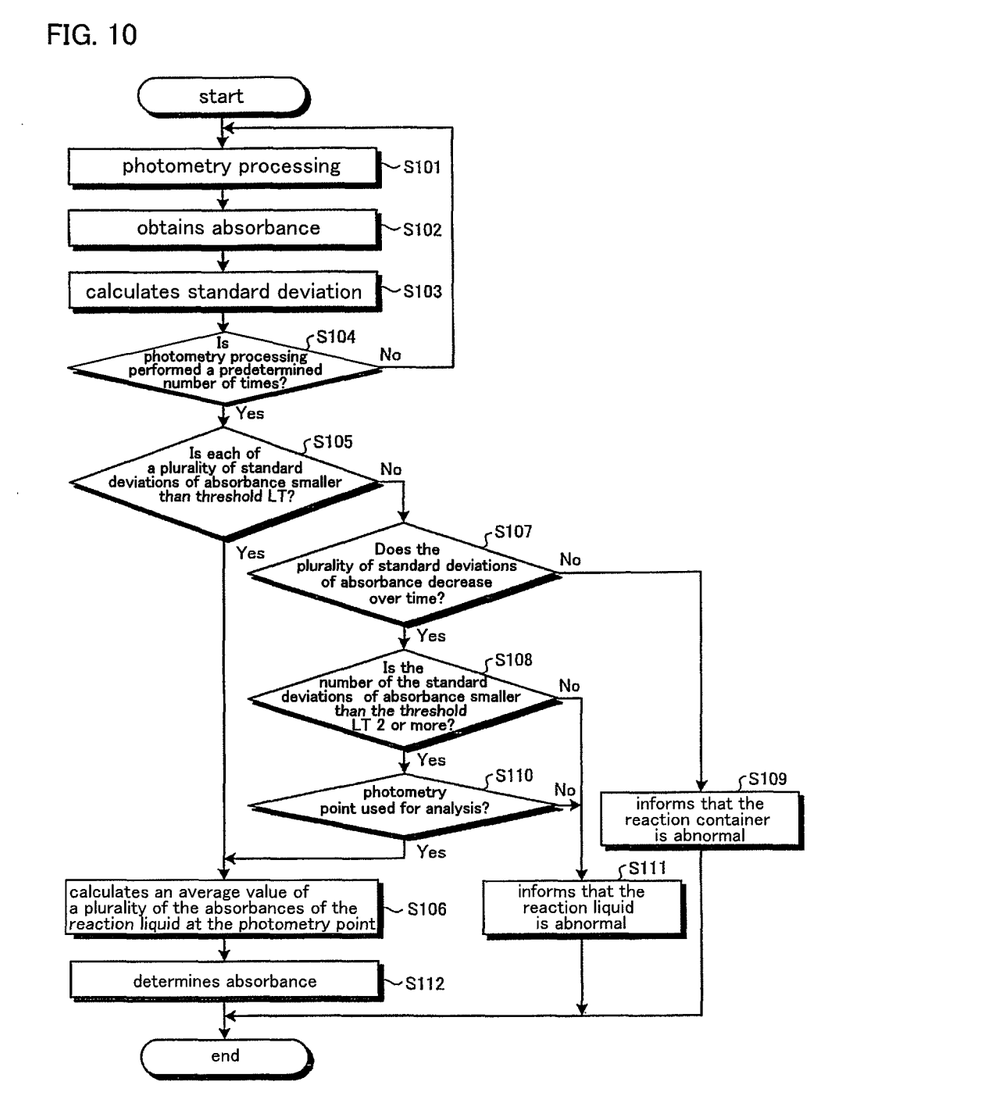
FIG. 10 is a flowchart illustrating an outline of processing for determining absorbance performed by a control section and a determination section of an automatic analyzer according to an embodiment of the present invention.

Hereinafter, processing for determining absorbance performed by the automatic analyzer 1 will be described with reference to the flowchart illustrated in FIG. 10. A course of processing will be described hereinafter in a case where processing for determining absorbance is performed for a sample after a second reagent is dispensed into a reaction container 20.

First, the photometry section 18 performs photometry processing for measuring, a plurality of times, absorbance of a reaction liquid W in a reaction container 20 at any one time the reaction container 20 passes in between the light source 18a and the light receiving section 18b (step S101).

Subsequently, the standard deviation calculating section 34a obtains a plurality of absorbances of the reaction liquid, measured by the photometry section 18 at any one time the reaction container 20 passes through the photometry section 18, from the recording section 35 via the control section 31 (step S102), and calculates a standard deviation of the absorbances (step S103).

Subsequently, the control section 31 judges as to whether or not photometry processing by the photometry section 18 has been performed a predetermined number of times with regard to the reaction container 20 passing through the photometry section 18 (step S104). If the photometry processing by the photometry section 18 has not been performed a predetermined number of times (step S104: No), then the processing proceeds to step S101. On the other hand, if the photometry processing by the photometry section 18 has been performed a predetermined number of times (step S104: Yes), then the processing proceeds to step S105.

Subsequently, the standard deviation judging section 34b judges as to whether each of a plurality of standard deviations of absorbance, calculated by the standard deviation calculating section 34a, is smaller than the threshold LT (step S105). If each of the plurality of standard deviations of absorbance is smaller than the threshold LT (step S105: Yes), then the processing proceeds to step S106. On the other hand, if each of the plurality of standard deviations of absorbance is not smaller than the threshold LT (step S105: No), then the processing proceeds to step S107.

At step S107, the abnormality specifying section 34e judges as to whether or not the plurality of standard deviations of absorbance, calculated by the standard deviation calculating section 34a, decrease over time (step S107). If the plurality of standard deviations of absorbance decrease over time (step S107: Yes), then the processing proceeds to step S108. On the other hand, if the plurality of standard deviations of absorbance do not decrease over time (step S107: No), then the processing proceeds to step S109, and the report processing section 34f allows the output section 36 to output information indicating that the reaction container 20 is abnormal, via the control section 31 (step S109), thus terminating the processing.

At step S108, the abnormality specifying section 34e judges as to whether the number of the standard deviations of absorbance smaller than the threshold LT is 2 or more (step S108). If the number of the standard deviations of absorbance smaller than the threshold LT is 2 or more (step S108: Yes), then the processing proceeds to step S110. On the other hand, if the number of the standard deviations of absorbance smaller than the threshold LT is less than 2 (step S108: No), then the processing proceeds to step S111.

At step S110, the abnormality specifying section 34e judges as to whether or not the photometry point with the standard deviation of absorbance smaller than the threshold LT is the photometry point used for the sample analysis (step S110). If the photometry point with the standard deviation of absorbance smaller than the threshold LT is the photometry point used for the sample analysis (step S110: Yes), then the processing proceeds to step S106. On the other hand, if the photometry point with the standard deviation of absorbance smaller than the threshold LT is not the photometry point used for the sample analysis (step S110: No), then the processing proceeds to step S111, and the report processing section 34f allows the output section 36 to output information indicating that the reaction liquid W is abnormal, via the control section 31 (step S111), thus terminating the processing.

At step S106, the average value calculating section 34c calculates an average value of a plurality of the absorbances of the reaction liquid at the photometry point with the standard deviation of absorbance which is judged to be smaller than the threshold LT by the standard deviation judging section 34b (step S106).

Subsequently, the absorbance determining section 34d determines a plurality of average values calculated by the average value calculating section 34c to be the absorbance used for the sample analysis (step S112), thus terminating the processing.

In the embodiment of the present invention, the photometry section 18 measures the absorbance of the reaction liquid W in a reaction container 20 a plurality of times at any one time the reaction container 20 passes in between the light source 18a and the light receiving section 18b; the standard deviation calculating section 34a calculates a standard deviation of the absorbance every time the reaction container 20 passes in between the light source 18a and the light receiving section 18b; the standard deviation judging section 34b judges as to whether or not each of the standard deviations of the absorbance is smaller than the threshold LT. Subsequently, the average value calculating section 34c calculates an average value of a plurality of absorbances of the reaction liquid W with a standard deviation of absorbance judged to be smaller than the threshold LT; and the absorbance determining section 34d determines any one of a plurality of average values to be the absorbance used for the sample analysis, thereby obtaining an analysis result using the reaction liquid W with absorbance appropriate for analysis processing. Further, since the abnormality specifying section 34e is configured to specify a cause of abnormality based on the chronological change in the standard deviation, a reaction container 20 with a scratch S2 is not used when the analysis is conducted again. Thereby, it allows one to prevent an abnormal value in an analysis result due to the scratch S2 on the reaction container 20, and as a result, it allows one to prevent the processing efficiency from being decreased in the series of the analysis processing.

According to the embodiment described above, in the case where the number of the standard deviations smaller than the threshold LT is 2 or more, anyone of average values of absorbances of the reaction liquid W measured a plurality of times by the photometry section 18 at any one time the reaction container 20, having the standard deviation smaller than the threshold LT, passes in between the light source 18a and the light receiving section 18b, is used as the absorbance used for the sample analysis. However, the number of the standard deviation less than the threshold LT may vary in accordance with an analysis method, an analysis category, a reagent or the like. For example, the number of the standard deviation less than the threshold LT may be 1 or more.

In addition, according to the embodiment described above, whether or not the standard deviation of absorbance is smaller than the threshold LT is judged after the second reagent is dispensed. However, the time for the judging may be adjusted in accordance with an analysis method, an analysis category, a reagent or the like. For example, the judging may be performed after the first reagent is dispensed.

Further, according to the embodiment described above, the average value of the absorbances of the reaction liquid W in the reaction container 20 measured a plurality of times by the photometry section 18 at any one time the reaction container 20 passes in between the light source 18a and the light receiving section 18b, is determined to be the absorbance used for the sample analysis. However, without limitation to this case, it is also possible to use the maximum value or minimum value of the absorbance of the reaction liquid W in the reaction container 20 measured a plurality of times by the photometry section 18 at any one time the reaction container 20 passes in between the light source 18a and the light receiving section 18b. Alternatively, it is also possible to use one of the plurality of absorbances of the reaction liquid.

Further, according to the embodiment described above, the abnormality specifying section 34e specifies that there is a scratch S2 on a reaction container 20 when the standard deviation of absorbance maintains a constant value while exceeding the threshold LT. However, without limitation to this case, it is also possible to specify such a case to be where there is a stain adhered to the reaction container 20, there is a gas bubble mixed in the reaction liquid W, or there is a foreign substance mixed in the reaction liquid W.

INDUSTRIAL APPLICABILITY

As described above, the automatic analyzer according to the present invention is useful for obtaining an analysis result using a reaction liquid with absorbance appropriate for analysis processing, and is suitable for automatic analyzers, in particular.

The invention claimed is:

1. An automatic analyzer for analyzing a sample by dispensing the sample and a reagent into a reaction container and using a reaction liquid combined in the reaction container, the automatic analyzer comprising:
    a reaction table for retaining a plurality of the reaction containers along the circumference, capable of rotating along the circumference;
    a photometry section for measuring absorbance of the reaction liquid in the reaction container a plurality of times at any one time the reaction container passes through a predetermined area with the rotation of the reaction table, which is performed every time the reaction container passes through the predetermined area;
    a standard deviation calculating section for calculating the standard deviation of a plurality of absorbances of the reaction liquid measured by the photometry section at any one time the reaction container passes through the predetermined area, which is performed every time the reaction container passes through the predetermined area;
    a standard deviation judging section for judging as to whether or not each of a plurality of the standard deviations calculated by the standard deviation calculating section is smaller than the threshold set based on the standard deviation of a plurality of absorbances in a homogeneously-stirred reaction liquid;
    an average value calculating section for calculating an average value for the plurality of absorbances for the reaction liquid having a standard deviation judged to be smaller than the threshold by the standard deviation judging section; and
    an absorbance determining section for determining any one of a plurality of average values calculated by the average value calculating section to be absorbance for performing a sample analysis.

2. The automatic analyzer according to claim 1, wherein the absorbance determining section determines absorbance when the plurality of standard deviations decrease over time and the number of standard deviations smaller than the threshold is 2 or more.

3. The automatic analyzer according to claim 1, further including an abnormality specifying section for specifying a cause of abnormality based on the change over time in the plurality of standard deviations.

4. The automatic analyzer according to claim 3, wherein the abnormality specifying section specifies that the reaction liquid of the reaction container is abnormal when the number of the standard deviations smaller than the threshold is 1 or below.

* * * * *